(12) United States Patent
Marashdeh et al.

(10) Patent No.: US 11,408,847 B2
(45) Date of Patent: Aug. 9, 2022

(54) EXTREME-CONDITION SENSORS FOR USE WITH ELECTRICAL CAPACITANCE VOLUME TOMOGRAPHY AND CAPACITANCE SENSING APPLICATIONS

(71) Applicants: Tech4Imaging LLC, Columbus, OH (US); Ohio State Innovation Foundation, Columbus, OH (US)

(72) Inventors: Qussai Marashdeh, Columbus, OH (US); Yousef Alghothani, Columbus, OH (US); Jesse Hudak, Columbus, OH (US); Geoffrey Legg, Tewksbury, MA (US); Benjamin Straiton, Pataskala, OH (US); Andrew Tong, Massillon, OH (US)

(73) Assignees: Tech4Imaging LLC, Columbus, OH (US); Ohio State Innovation Foundation, Columbus, OH (US)

( * ) Notice: Subject to any disclaimer, the term of this patent is extended or adjusted under 35 U.S.C. 154(b) by 190 days.

(21) Appl. No.: 16/621,794

(22) PCT Filed: May 30, 2018

(86) PCT No.: PCT/US2018/035041
§ 371 (c)(1),
(2) Date: Dec. 12, 2019

(87) PCT Pub. No.: WO2018/231517
PCT Pub. Date: Dec. 20, 2018

(65) Prior Publication Data
US 2021/0010966 A1    Jan. 14, 2021

Related U.S. Application Data

(60) Provisional application No. 62/518,785, filed on Jun. 13, 2017.

(51) Int. Cl.
*G01R 27/26*    (2006.01)
*G01N 27/22*    (2006.01)
*A61B 5/0536*   (2021.01)

(52) U.S. Cl.
CPC ......... *G01N 27/226* (2013.01); *A61B 5/0536* (2013.01)

(58) Field of Classification Search
CPC ........................... G01N 27/226; A61B 5/0536
(Continued)

(56) References Cited

U.S. PATENT DOCUMENTS 8,614,707 B2   12/2013   Warsito et al.
10,073,050 B2   9/2018   Bruere et al.
(Continued)

FOREIGN PATENT DOCUMENTS

CN    101025404 A    8/2007
CN    102364420 A    2/2012

OTHER PUBLICATIONS

CN 102364420 Machine Translation, Feb. 29, 2012 (Year: 2012).*
WO 2016071635 Machine Translation (Year: 2016).*
CN 101025404 Machine Translation, Aug. 29, 2007 (Year: 2007).*

*Primary Examiner* — Raul J Rios Russo
(74) *Attorney, Agent, or Firm* — Standley Law Group LLP; James L. Kwak; Stephen L. Grant

(57) ABSTRACT

An electrical capacitance volume tomography sensor for use in high temperature, high pressure applications for measuring or imaging a flow within the sensor, the sensor comprising an outer pressure vessel, a plurality of electrodes placed within the outer pressure vessel, a plurality of threaded studs, wherein one of the threaded studs is attached to one of the plurality of electrodes, a coating or layer is placed on the plurality of electrodes for electrically isolating the plurality of electrodes, a plurality of holes in the outer pressure vessel for allowing terminal connections to the
(Continued)

plurality of electrodes within the outer pressure vessel, wherein each of the plurality of holes accepts one of the plurality of threaded studs, and a plurality of gaskets, where one gasket is placed at each of the plurality of holes to seal the pressure at each of the holes in the outer pressure vessel by placing one gasket concentric around one threaded stud and conforming each gasket between a back of an electrode and the inside wall of the pressure vessel by tightening each of the plurality of nuts on each of the threaded studs.

25 Claims, 4 Drawing Sheets

(58) Field of Classification Search
USPC ... 324/76.11–76.83, 459, 600, 649, 658, 663
See application file for complete search history.

(56) References Cited

U.S. PATENT DOCUMENTS

| | | | | |
|---|---|---|---|---|
| 2001/0041154 | A1* | 11/2001 | Murata | C01B 13/11 422/186.3 |
| 2002/0191970 | A1* | 12/2002 | Raghavan | F28F 7/02 392/479 |
| 2015/0355126 | A1 | 12/2015 | Voutilainen et al. | |
| 2016/0101996 | A1* | 4/2016 | Casbeer | C02F 1/463 205/744 |
| 2017/0328853 | A1 | 11/2017 | Marashdeh et al. | |
| 2018/0252832 | A1* | 9/2018 | Smoot | G01D 5/2405 |
| 2019/0372449 | A1* | 12/2019 | Mills | H02K 44/085 |

* cited by examiner

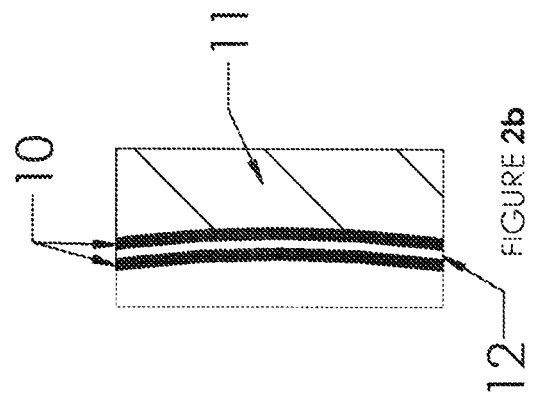
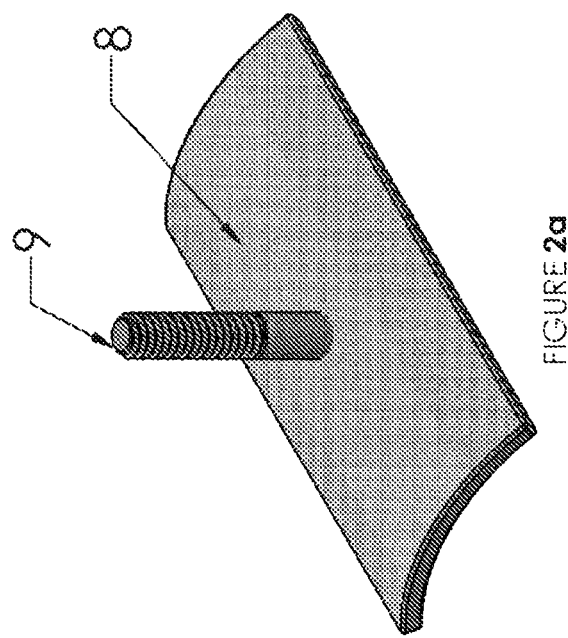

SECTION A-A

DETAIL J

US 11,408,847 B2

EXTREME-CONDITION SENSORS FOR USE WITH ELECTRICAL CAPACITANCE VOLUME TOMOGRAPHY AND CAPACITANCE SENSING APPLICATIONS

BACKGROUND OF THE INVENTIVE FIELD

Electrical Capacitance Volume Tomography (ECVT) is the non-invasive volumetric image reconstruction of materials in the imaging domain utilizing 3D features in the capacitance sensor design. An ECVT system is generally comprised of a sensor, data acquisition system, computer system and software for reconstruction of the 3D image representing the volume inspected by the sensor. An ECVT sensor is generally comprised of a plurality (n) of electrodes or plates placed around or near a region of interest, which, in one embodiment, provides n(n−1)/2 independent capacitance measurements which are used for image reconstruction. Capacitance data collected from the electrodes or plates placed around or near the region of interest are used to achieve the image reconstruction. ECVT technology is described in U.S. Pat. No. 8,614,707 to Warsito et al. which is hereby incorporated by reference.

ECVT applications span a wide array of industries. ECVT has been most recently applicable to multiphase flow applications commonly employed in many industrial processes, but may also be applied to single phase and stationary applications that require non-invasive imaging, measuring, or monitoring.

In ECVT, sensor plates are generally distributed around the circumference or along the edge of a vessel under interrogation. If the plates are along the outside of the vessel, the vessel itself should not be an electrical conductor in order for the electric field to penetrate the region of interest. This presents a challenge in high pressure and high temperature applications where such high pressure high temperature vessels are usually made of steel or other electrical conductors.

In order to overcome this challenge, the present invention involves a non-invasive ECVT sensor that can withstand extreme environments including high pressure, high temperature, highly abrasive, and highly corrosive environments.

SUMMARY OF THE GENERAL INVENTIVE CONCEPT

The design of the present invention involves an arrangement of capacitance plates within an outer vessel that can contain high pressures while operating at high temperatures. The plates are isolated from the flow and from the outer pressure vessel by a coating. The coating is electrically insulative or has sufficiently high impedance to electrically isolate the capacitance plates. The coating and the plates are each independently highly resistant to high temperature, highly abrasive, and highly corrosive environments.

In one embodiment of the invention, the invention is an electrical capacitance volume tomography sensor for use in high temperature, high pressure applications for measuring or imaging a flow within the sensor, the sensor comprising: an outer pressure vessel, having an inner wall and outer wall; a plurality of electrodes placed within the outer pressure vessel; a plurality of threaded studs, wherein one of the threaded studs is attached to one of the plurality of electrodes; a plurality of nuts for engagement to the plurality of threaded studs; a coating or layer is placed on the plurality of electrodes for electrically isolating the plurality of electrodes; a plurality of holes in the outer pressure vessel for allowing terminal connections to the plurality of electrodes within the outer pressure vessel, wherein each of the plurality of holes accepts one of the plurality of threaded studs; and a plurality of gaskets, where one gasket is placed at each of the plurality of holes to seal the pressure at each of the holes in the outer pressure vessel by placing one gasket concentric around one threaded stud and conforming each gasket between a back of an electrode and the inside wall of the pressure vessel by tightening each of the plurality of nuts on each of the threaded studs. In another embodiment, the studs are not threaded and engage a fastener adapted to tighten against the stud.

The design of the present invention involves a method to seal the pressure of the vessel while allowing electrical connections to bridge from the interior of the vessel to the exterior of the vessel.

The design of the present invention allows the ECVT sensor to remain non-invasive. The inner diameter of the sensor matches or closely matches the inner diameter of the process flow vessels, eliminating disruption of flow.

The design of the present invention involves modularity of the sensor, allowing for various numbers, configurations, and spacing of plates.

The design of the present invention allows for the replacement of individual plates should the need arise.

The design of the present invention allows the sensor to be scalable to accommodate any vessel size or geometry.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1b illustrates one embodiment of the capacitance plates layout of the sensor in FIG. 1a;

FIG. 1a illustrates another embodiment of the capacitance plates layout with a grounding matrix;

FIG. 2a illustrates one embodiment of the capacitance plate design of the present invention;

FIG. 2b illustrates a cross section of another embodiment of the capacitance plate design of the present invention;

FIG. 3b illustrates a cross section of the embodiment in FIG. 3a;

DETAILED DESCRIPTION OF THE DRAWINGS

The following detailed description of the exemplary embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1B:
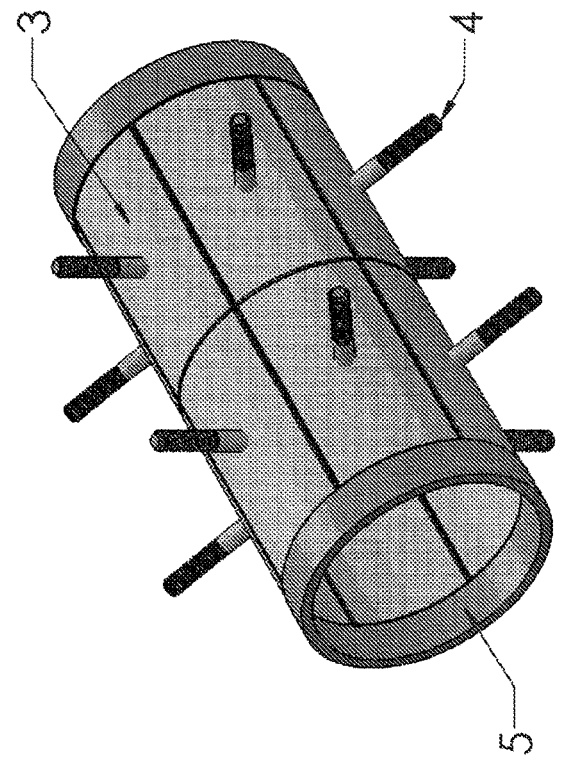
Figure 1C:
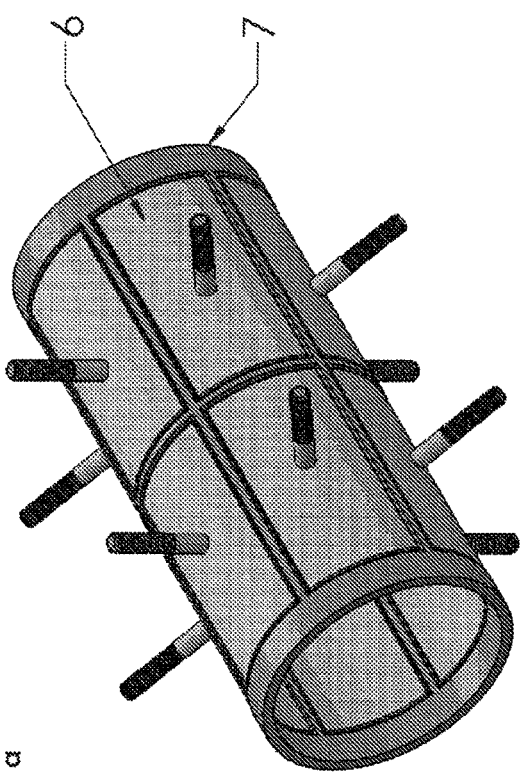
Figure 1A:
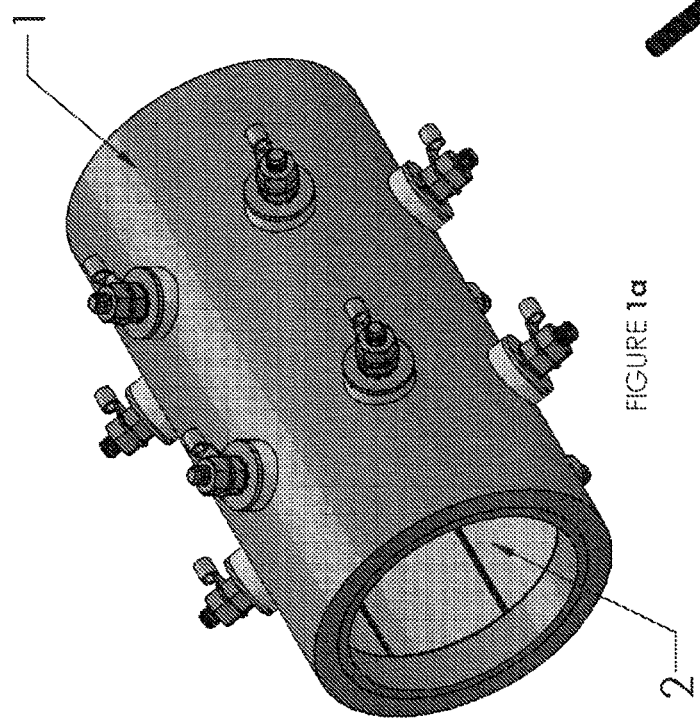
FIG. 1a illustrates one embodiment of a high pressure, high temperature sensor design of the present invention.

FIG. 1a illustrates one embodiment of a high pressure, high temperature sensor design of the present invention. The design involves an outer pressure vessel (1) that will contain the high pressure environment within the sensor. The capacitance plates (2) are nestled within and against the outer pressure vessel. The high pressures within the sensor will be transmitted through the capacitance plates and contained by the outer pressure vessel. In this embodiment there are holes in the outer pressure vessel that allow the terminal connections to the capacitance plates to be transmitted through to the outside. In this embodiment a gasket is used to seal the pressure at the hole in the outer pressure vessel by placing it concentric around the stud welded to the electrode plate and conforming the gasket between the back of the plate and the inside of the pressure vessel by tightening a nut on the threaded stud. The gasket may be replaced by and O-ring and ring grove, liquid sealant, or other mechanical means to seal the pressure at the signal port holes. In one embodiment, the outer pressure vessel is standard steel piping with through-holes drilled in for plate terminals to pass through.

FIG. 1b illustrates the embodiment in FIG. 1a with the outer pressure vessel and terminal hardware removed, revealing the inner capacitance plates (3) with their terminal connectors (4). In this embodiment, the plates fit flush with one another to create the inner vessel that matches or closely matches the inner diameter of the process flow. In this embodiment spacers (5) are used to streamline the flow.

FIG. 1c illustrates a different embodiment of a capacitance plates layout that can be used with the same outer pressure vessel of FIG. 1a. In this embodiment, the capacitance plates (6) are smaller and are spaced apart. There is a matrix (7) that serves to streamline the inner vessel and provide a grounding signal between the capacitance plates, if necessary. This figure helps illustrate the modularity of the present invention; capacitance plates can be replaced, different arrangements can be made out of any number of plates with a minimum of two plates, and plates can even be added, with or without modifying the outer pressure vessel.

FIG. 2a illustrates one embodiment of a capacitance plate design of the present invention. The plate itself should be conductive. In this embodiment, the plate is isolated via coating, overmolding, deposition, mechanical encasing, or otherwise surrounding with a layer (8) that isolates each plate from one another, from the flow, and from the outer pressure vessel. In this embodiment, the coating is electrically insulative or has a high impedance, is highly abrasion resistant, and highly corrosion resistant. In this embodiment, the end of the terminal connector (9) is left uncoated to allow for connection to the signal cables. In one embodiment, the curved plate is manufactured out of steel and a threaded rod is welded onto the back. Different metals and other conductive materials may be used to make the plate and the terminal connector. The plate can then be coated with a variety of dielectric materials depending on the application, including ceramics and high temperature plastics.

FIG. 2b illustrates the cross section of one embodiment of an electrode plate (12) coated with a thin layer of dielectric (10), as it is installed against the steel shell of the sensor (11).

Figure 3B:
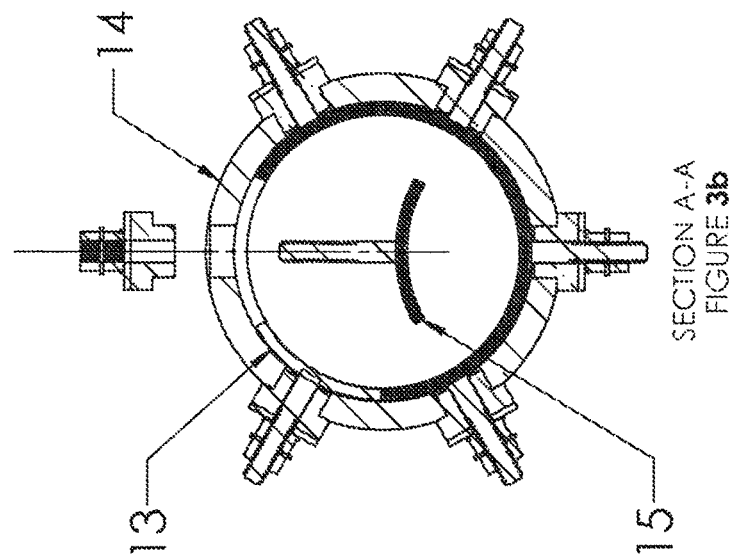
Figure 3C:
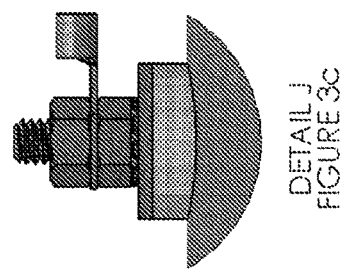
FIG. 3c illustrates a detailed view of one embodiment of the terminal connections to the capacitance plates.
Figure 3A:
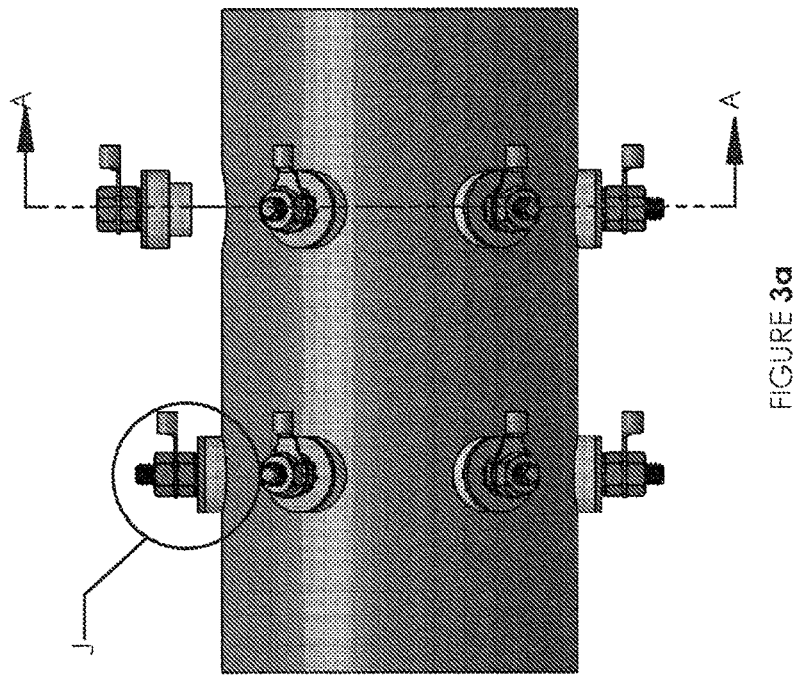
FIG. 3a illustrates a side view of one embodiment of the sensor design of the present invention.

FIG. 3a illustrates a side view of one embodiment of sensor design of the present invention. FIG. 3b illustrates a cross section of the embodiment in FIG. 3a. This figure helps illustrate how the capacitance plates (13) in this embodiment are nestled against the outer pressure vessel (14). Any pressure within the region will be transmitted through the plates and contained by the outer vessel. The figure also illustrates a plate (15) prior to assembly on the inside of the pressure vessel.

FIG. 3c illustrates a detailed view of one embodiment of the terminal connections to the capacitance plates. In this embodiment standard hardware is used to tighten the capacitance plates, via their threaded studs, up against the inside of the pressure vessel.

Figure 4:
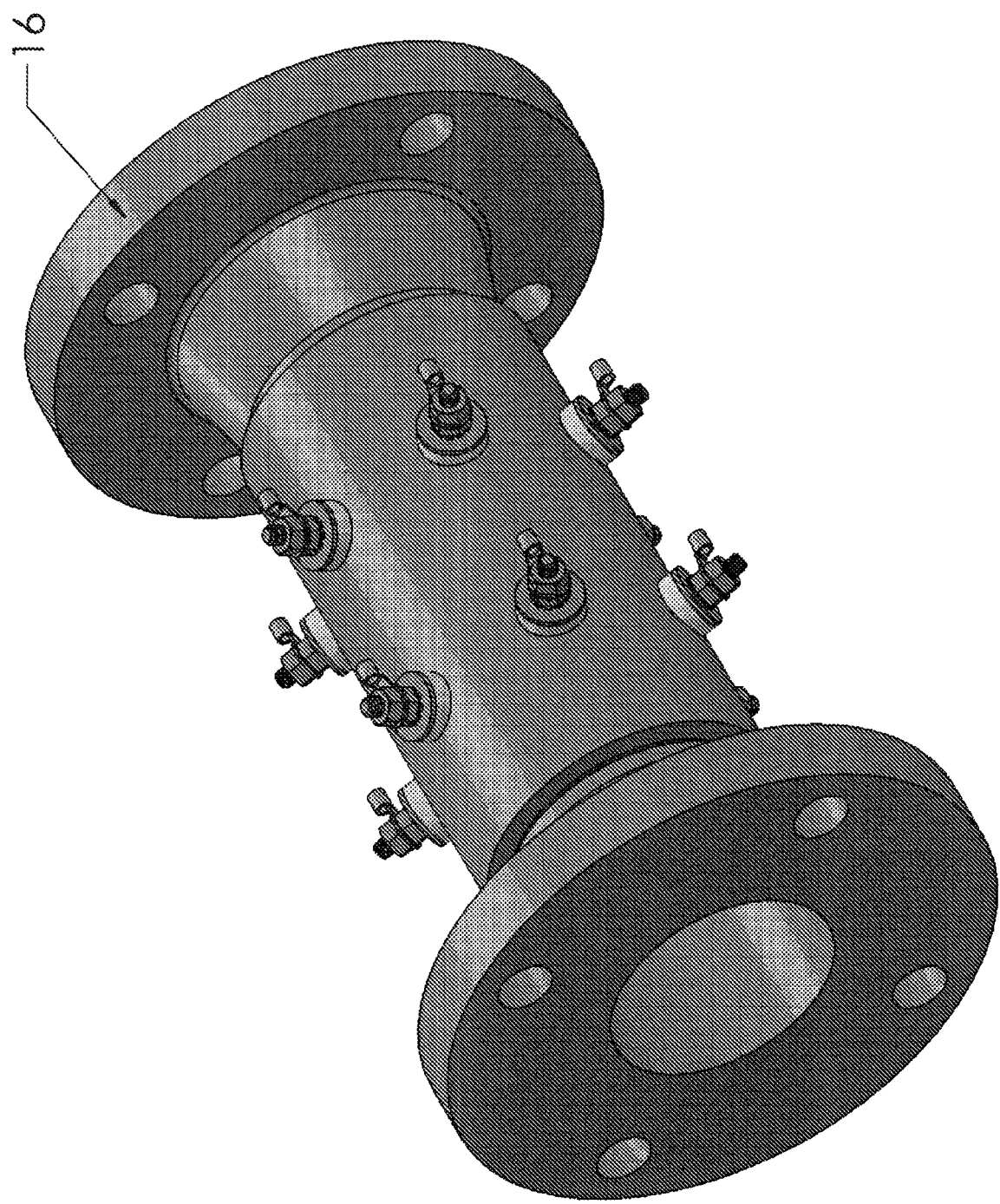
FIG. 4 illustrates the embodiment in FIG. 3a with flanges attached.

FIG. 4 illustrates the embodiment in FIG. 3a with flanges attached. Standard or custom pipe flanges (16) can be attached to the sensor in order to incorporate the sensor into the necessary pipeline.

While certain embodiments of the present invention are described in detail above, the scope of the invention is not to be considered limited by such disclosure, and modifications are possible without departing from the spirit of the invention.

What is claimed is:

1. An electrical capacitance volume tomography (ECVT) sensor for use in high temperature, high pressure applications for measuring or imaging a flow within the (ECVT) sensor, the (ECVT) sensor comprising:
   an outer pressure vessel, having an inner wall and outer and a diameter;
   a plurality of electrodes placed within the outer pressure vessel, wherein the plurality of electrodes are adapted to fit together to create an inner vessel that closely matches an inner diameter of the flow within the ECVT sensor and wherein the inner vessel is contained within and adjacent to the outer pressure vessel and wherein the inner vessel has a diameter smaller than the diameter of the outer pressure vessel; and
   wherein the electrodes are modular and are adapted to be replaced without modifying the outer pressure vessel;
   a plurality of threaded studs, wherein one of the threaded studs is attached to one of the plurality of electrodes;
   a plurality of nuts for engagement to the plurality of threaded studs;
   a coating or layer is placed on the plurality of electrodes for electrically isolating the plurality of electrodes;
   a plurality of holes in the outer pressure vessel for allowing terminal connections to the plurality of electrodes within the outer pressure vessel, wherein each of the plurality of holes accepts one of the plurality of threaded studs.

2. An apparatus according to claim 1, wherein the outer pressure vessel is a steel pipe.

3. An apparatus according to claim 1, further comprising: a plurality of gaskets, where one gasket is placed at each of the plurality of holes to seal the pressure at each of the holes in the outer pressure vessel by placing one gasket concentric around one threaded stud and conforming each gasket between a back of an electrode and the inside wall of the pressure vessel by tightening each of the plurality of nuts on each of the threaded studs.

4. An apparatus according to claim 1, wherein the plurality of electrodes are placed around the inner wall of the outer pressure vessel; and wherein the threaded studs are adapted to be used to tighten the electrodes against the inner wall of the outer pressure vessel.

5. An apparatus according to claim 4, wherein the plurality of electrodes are flush with each other and separated by spacers.

6. An apparatus according to claim 1, wherein liquid sealant, or other mechanical means, is used to seal the pressure at each of the plurality of holes.

7. An apparatus according to claim 1, further comprising a matrix to streamline the outer pressure vessel and provide a grounding signal between the plurality of electrodes.

8. An apparatus according to claim 1, wherein the coating or layer electrically isolates each plate from one another, from the flow, and from the outer pressure vessel.

9. An apparatus according to claim 1, wherein the plurality of electrodes are highly resistant to high temperature, highly corrosive, environments.

10. An apparatus according to claim 1, wherein the outer pressure vessel may be opened to access and remove the plurality of electrodes.

11. An apparatus according to claim 1, further comprising a first flange attached to one end of the outer pressure vessel and a second flange attached to a second end of the outer pressure vessel.

12. An apparatus according to claim 1, further comprising:
a thin layer of dielectric applied to each of the plurality of electrodes.

13. An electrical capacitance volume tomography (ECVT) sensor for use in high temperature, high pressure applications for measuring or imaging a flow within the (ECVT) sensor, the (ECVT) sensor comprising:
an outer pressure vessel, having an inner wall and outer wall and a diameter;
a plurality of electrodes placed within the outer pressure vessel, wherein the plurality of electrodes are adapted to fit together to create an inner vessel that closely matches an inner diameter of the flow within the ECVT sensor and wherein the inner vessel is contained within and adjacent to the outer pressure vessel and wherein the inner vessel has a diameter smaller than the diameter of the outer pressure vessel; and
wherein the electrodes are modular and are adapted to be replaced without modifying the outer pressure vessel;
a plurality of studs, wherein one of the studs is attached to one of the plurality of electrodes;
a plurality of fasteners for engagement to the plurality of threaded studs;
a coating or layer is placed on the plurality of electrodes for electrically isolating the plurality of electrodes;
a plurality of holes in the outer pressure vessel for allowing terminal connections to the plurality of electrodes within the outer pressure vessel, wherein each of the plurality of holes accepts one of the plurality of threaded studs.

14. An apparatus according to claim 13, wherein the outer pressure vessel is a steel pipe.

15. An apparatus according to claim 13, further comprising: a plurality of gaskets, where one gasket is placed at each of the plurality of holes to seal the pressure at each of the holes in the outer pressure vessel by placing one gasket concentric around one threaded stud and conforming each gasket between a back of an electrode and the inside wall of the pressure vessel by tightening each of the plurality of fasteners on each of the threaded studs.

16. An apparatus according to claim 13, wherein the plurality of electrodes are placed around the inner wall of the outer pressure vessel; and
wherein the threaded studs are adapted to be used to tighten the electrodes against the inner wall of the outer pressure vessel.

17. An apparatus according to claim 13, wherein the plurality of electrodes are flush with each other and separated by spacers.

18. An apparatus according to claim 13, further comprising:
a plurality of O-rings, one O-ring placed at each of the plurality of holes, to seal the pressure at each of the plurality of holes.

19. An apparatus according to claim 13, further comprising a matrix to streamline the outer pressure vessel and provide a grounding signal between the plurality of electrodes.

20. An apparatus according to claim 13, wherein the coating or layer electrically isolates each plate from one another, from the flow, and from the outer pressure vessel.

21. An apparatus according to claim 13, wherein the plurality of electrodes are highly resistant to high temperature, highly corrosive, environments.

22. An apparatus according to claim 13, wherein the outer pressure vessel may be opened to access and remove the plurality of electrodes.

23. An apparatus according to claim 13, further comprising a first flange attached to one end of the outer pressure vessel and a second flange attached to a second end of the outer pressure vessel.

24. An apparatus according to claim 13, further comprising:
a thin layer of dielectric applied to each of the plurality of electrodes.

25. An electrical capacitance volume tomography (ECVT) sensor for use in high temperature, high pressure applications for measuring or imaging a flow within the (ECVT) sensor, the (ECVT) sensor comprising:
an outer pressure vessel, having an inner wall and outer wall and a diameter;
a plurality of electrodes placed within the outer pressure vessel, wherein the plurality of electrodes are adapted to fit together to create an inner vessel that closely matches an inner diameter of the flow within the ECVT sensor and wherein the inner vessel is contained within and adjacent to the outer pressure vessel and wherein the inner vessel has a diameter smaller than the diameter of the outer pressure vessel; and
wherein the electrodes are modular and are adapted to be replaced without modifying the outer pressure vessel;
a plurality of threaded studs, wherein one of the threaded studs is attached to one of the plurality of electrodes;
a plurality of nuts for engagement to the plurality of threaded studs;
a coating or layer is placed on the plurality of electrodes for electrically isolating the plurality of electrodes;
a plurality of holes in the outer pressure vessel for allowing terminal connections to the plurality of electrodes within the outer pressure vessel, wherein each of the plurality of holes accepts one of the plurality of threaded studs; and
a plurality of gaskets, where one gasket is placed at each of the plurality of holes to seal the pressure at each of the holes in the outer pressure vessel by placing one gasket concentric around one threaded stud and conforming each gasket between a back of an electrode and the inside wall of the pressure vessel by tightening each of the plurality of nuts on each of the threaded studs.

\* \* \* \* \*

UNITED STATES PATENT AND TRADEMARK OFFICE
CERTIFICATE OF CORRECTION

| | |
|---|---|
| PATENT NO. | : 11,408,847 B2 |
| APPLICATION NO. | : 16/621794 |
| DATED | : August 9, 2022 |
| INVENTOR(S) | : Marashdeh et al. |

It is certified that error appears in the above-identified patent and that said Letters Patent is hereby corrected as shown below:

In the Specification

In Column 2, Line 47, please delete "FIG. 1a" and insert -- FIG. 1c --.

In the Claims

In Column 4, Line 24, Claim 1, please delete "having an inner wall and outer" and insert -- having an inner wall and outer wall --.

Signed and Sealed this
Twentieth Day of September, 2022

*Katherine Kelly Vidal*

Katherine Kelly Vidal
*Director of the United States Patent and Trademark Office*